United States Patent [19]

Vodrazka et al.

[11] 4,366,326
[45] Dec. 28, 1982

[54] OXYALKYLATED FATTY ALCOHOLS HAVING END GROUPS BLOCKED BY REACTION WITH PROPYLENE

[75] Inventors: Wolfgang Vodrazka, Freinsheim; Erhard Klahr, Ludwigshafen; Knut Oppenlaender, Ludwigshafen; Wolfgang Trieselt, Ludwigshafen; Dieter Stoeckigt, Ludwigshafen; Werner Neumann, Reilingen, all of Fed. Rep. of Germany

[73] Assignee: BASF Aktiengesellschaft, Rheinland-Pfalz, Fed. Rep. of Germany

[21] Appl. No.: 241,104

[22] Filed: Mar. 6, 1981

[51] Int. Cl.³ .................. C07C 43/00; C07C 41/03
[52] U.S. Cl. .................. 568/613; 518/618; 518/625; 252/174.21; 252/174.22
[58] Field of Search .................. 568/613, 618; 252/174.21, 174.22

[56] References Cited

U.S. PATENT DOCUMENTS 3,281,475 10/1966 Boettner et al. .................. 568/609
4,187,384 2/1980 Platz et al. .................. 568/618

Primary Examiner—Howard T. Mars
Attorney, Agent, or Firm—Oblon, Fisher, Spivak, McClelland & Maier

[57] ABSTRACT

Compounds of the formula I

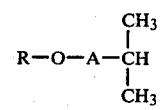

where R is $C_8$–$C_{20}$-alkyl and A is a polyalkylene oxide radical composed of from 4 to 30 alkylene oxide units, of which from 100 to 60 mole % are ethylene oxide units and from 0 to 40 mole % are 1,2-propylene oxide units or 1,2-butylene oxide units or a mixture of these.

1 Claim, No Drawings

OXYALKYLATED FATTY ALCOHOLS HAVING END GROUPS BLOCKED BY REACTION WITH PROPYLENE

The present invention relates to novel oxyalkylated fatty alcohols whose end groups are blocked by reaction with propylene.

The reaction of olefins, inter alia propylene, with polyethylene glycols, ie. with pure ethylene oxide polymers or with their monomethyl ethers, in the presence of an acidic ion exchanger, is disclosed in German Published Applications Nos. DAS 2,801,793 and DAS 2,544,569. It gives polyethylene glycols, or polyethylene glycol methyl ethers, which have blocked end groups. German Published Application No. DAS 1,520,647 discloses oxyethylates of higher alcohols, in which the end groups have been blocked by reaction with isobutylene or higher tertiary olefins. This DAS specifically states (see column 5, lines 38 et seq.) that the reaction of oxyethylated higher alcohols with secondary olefins, eg. propylene, takes place to only a very slight degree, if at all, and that the formation of corresponding secondary alkyl ethers is not detectable analytically.

The oxyethylated alcohols, with terminal groups blocked by tertiary alkyl, described in German Published Application Nos. DAS 1,520,647 are, according to the said DAS, stable to alkali and low-foaming; however, they are not stable to acids, since the ether bond is cleaved in acid media.

It is an object of the present invention to provide surfactants which have blocked end groups and which in addition to possessing the above properties are also stable to acids, thereby allowing them to be used, for example, in acidic liquors in industrial cleaning agents.

We have found that this object is achieved, surprisingly, by providing compounds of the formula I

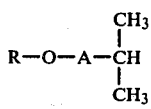 I where R is $C_8$–$C_{20}$-alkyl and A is a polyalkylene oxide radical composed of from 4 to 30 alkylene oxide units, of which from 100 to 60 mole % are ethylene oxide units and from 0 to 40 mole % are 1,2-propylene oxide units or 1,2-butylene oxide units or a mixture of these.

In view of the fact that the corresponding tert.-alkyl polyalkylene glycol ethers are not stable to acids, the novel sec.-alkyl ethers represent a surprising advance in the field of non-ionic surfactants of this type of structure. Furthermore, it is surprising that the reaction of the oxyalkylated higher alcohols with propylene, similar to the reaction which has hitherto only been achieved with pure polyethylene glycols or their monomethyl ethers, should be possible at all, since German Published Application Nos. DAS 1,520,647 has unambiguously ruled out such a reaction.

Suitable starting compounds for the preparation of the products according to the invention, of the formula I, are higher alcohols of 8 to 20 carbon atoms, or mixtures of such alcohols, which have been oxyalkylated with from 4 to 30 alkylene oxide units.

The alcohols on which the compounds are based are as a rule saturated alcohols which preferably have very little branching; they may be either natural or synthetic alcohols, or mixtures of such alcohols. Specific examples are octanol, nonanol, decanol, dodecanol, tetradecanol, hexadecanol, octadecanol (stearyl alcohol), mixtures of these, and synthetic alcohol mixtures obtained by the oxo process or the Ziegler process, eg. $C_9/C_{11}$- and $C_{13}/C_{15}$-oxo-alcohols and $C_8/C_{10}$-, $C_{12}/C_{14}$- and $C_{16}/C_{20}$-Ziegler alcohols.

These alcohols are oxyalkylated with from 4 to 30, preferably from 5 to 15, ethylene oxide, 1,2-propylene oxide and/or 1,2-butylene oxide units, with the proviso that, as stated in the definition, the polyalkylene oxide block comprises from 100 to 60 mole % of ethylene oxide units from 0 to 40 mole % of propylene oxide and/or butylene oxide units, propylene oxide units being preferred.

Preferably, however, the polyalkylene oxide block consists exclusively of ethylene oxide units. If propylene oxide and/or butylene oxide units are also present, the polyalkylene oxide blocks may contain the individual alkylene oxide units in random distribution (such compounds being prepared by treatment with a mixture of the gaseous alkylene oxides) or in the form of individual blocks (such compounds being prepared by stepwise oxyalkylation with the individual alkylene oxides). The oxyalkylation operations are known and do not require special explanation.

The further reaction of the resulting oxyalkylates with propylene is in principle carried out in accordance with the methods disclosed in the above German Published Applications Nos. DAS 2,544,569 and DAS 2,801,793. In these, the oxyalkylated alcohol, or a mixture of such oxyalkylated products, is reacted, at from 50° to 170° C., preferably from 100° to 150° C., with an equimolar amount or, preferably, an excess of propylene, under from 1 to 100 bar, in a pressure vessel (for batchwise operation) or a pressure-tube reactor (for continuous operation), in the presence of an acidic catalyst.

Particularly suitable catalysts are strongly acidic ion exchangers. More especially, such strongly acidic ion exchangers may be crosslinked styrene/divinylbenzene copolymers possessing sulfo groups, for example the products sold under the registered tradenames ®LEWATIT SPC 118 H, LEWATIT SPC 108 H, ®AMBERLITE 200 and ®AMBERLYST 15.

The reaction mixture contains from about 1 to 30% by weight, preferably from 5 to 20% by weight, of the catalyst, based on oxyalkylated alcohol.

The reaction can be carried out in the absence of a solvent, under the autogenous pressure of the propylene, or in the presence of an inert solvent, ie. a solvent which does not engage in the chemical reaction under the conditions employed. Such solvents, which in some cases are an advantageous means of suspending the catalyst, in general have boiling points of from 35° to 200° C.; examples includes diethyl, ether, cyclohexane and tetrahydrofuran.

The pressure under which the reaction takes place depends on the chosen reaction temperature and on the desired reaction time, which may be from one to 30 hours and in turn depends on the nature of the oxyalkylate employed. The product is worked up by filtering off the catalyst and then stripping off unconverted propylene, and the small amounts of by-products formed, such as propylene oligomers, in a stream of inert gas. The products can be characterized by, for example, their molecular weight, cloud point, acid number and OH number.

The products according to the invention are low-foaming surfactants which are stable to alkalis and acids. They are, in particular, suitable for use in industrial cleaning processes, such as bottlewashing. They are employed, like other, conventional surfactants, in amounts of from 0.01 to 5% by weight, preferably from 0.1 to 3% by weight, based on liquor.

In addition to being stable to acids, the novel products exhibit a better wetting action than the isobutyl ethers of German Published Application No. DAS 1,520,647, thus making it possible to use, in liquors, the relatively small amounts mentioned above. The biological degradability of the products also conforms to current requirements in the Federal Republic of Germany (BGBl. 1977, Part I, page 244 et seq.).

The Examples which follow illustrate the invention. Parts are parts by weight, unless expressly stated otherwise, and bear the same relation to parts by volume as that of the kilogram to the liter.

EXAMPLE 1

550 parts of an adduct of a $C_{13}$–$C_{15}$-alcohol with 7 moles of ethylene oxide, 450 parts of propylene and 80 parts of a sulfonated styrene/divinylbenzene copolymer, trademark ®LEWATIT SPC 118 H, were stirred for 3 hours at 115° C., under autogenous pressure, in an autoclave having a capacity of 2,500 parts by volume.

After completion of the reaction, unconverted propylene was removed from the system by flashing off, the acidic ion exchanger was filtered off and low-boiling constituents (130 parts) were removed by distillation. The residue (580 parts) still contained 5.5 mole % of the oxyethylated starting material.

EXAMPLE 2

150 parts/h of an adduct of a $C_{13}$/$C_{15}$-alcohol with 8 moles of ethylene oxide, and 100 parts/h of propylene, were passed continuously, at 115° C. and 30 bar, through a pressure tube packed with a fixed bed of 2,400 parts by volume of the ion exchanger used in Example 1, the exchanger having been swollen in the oxyethylated $C_{13}$–$C_{15}$-alcohol. The mixture was released to atmospheric pressure at the reactor outlet. The liquid mixture obtained was freed from low-boiling constituents by distillation. The residue (165 parts/h) still contained 5.2 mole % of the oxyethylated starting material.

Oxyethylated alcohol with the end groups not blocked, and oxyethylated alcohol with the end groups blocked by reaction with butylene, were tested for comparison. The test methods were as follows:

Cloud point: DIN 53,917.
Foam (foam-beating method): DIN 53,902.
Wetting power: DIN 53,901, using 2g/l of surfactant, at room temperature.

The results obtained with the surfactants are as shown in the Tables which follow.

TABLE 1

| Substance | Cloud point [°C.] | Foam [cm] | Wetting power [sec] |
|---|---|---|---|
| Example 1 | 0 | 0 | 8 |
| Example 1 without blocking of end groups | 60 | 340 | 11 |
| Example 2 | 38 | 20 | 7 |
| Example 2 without blocking of end groups | 52 | 220 | 10 |

TABLE 2

| | immediate foam + 4% of $H_2SO_4$ | after 100 hours at 65° C. foam + 4% of $H_2SO_4$ | immediate foam + 10% of $H_2SO_4$ | after 100 hours at 65° C. foam + 10% of $H_2H_2SO_4$ |
|---|---|---|---|---|
| $C_{13/15}$-oxo-alcohol + 7 EO[x] + propylene (Example 1) | 0 cm | 0 cm | 0 cm | 0 cm |
| $C_{13/15}$-oxo-alcohol + 7 EO + butylene | 10 cm | 50 cm | 10 cm | 70 cm |
| $C_{13/15}$-oxo-alcohol + 8 EO + propylene (Example 2) | 30 cm | 30 cm | 30 cm | 30 cm |
| $C_{13/15}$-oxo-alcohol + 8 EO + butylene | 60 cm | 110 cm | 60 cm | 150 cm |

[x]Ethylene oxide

We claim:
1. A compound of the formula I

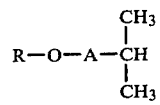

where R is $C_8$–$C_{20}$-alkyl and A is a polyethylene oxide radical composed of from 5 to 15 ethylene oxide units.

* * * * *